United States Patent [19]

Takaya et al.

[11] Patent Number: 4,705,851

[45] Date of Patent: Nov. 10, 1987

[54] PROCESS FOR THE PREPARATION OF 3-PHOSPHONIUMMETHYL-3-CEPHEM COMPOUNDS

[75] Inventors: Takao Takaya, Kawanishi; Hisashi Takasugi, Osaka; Takashi Masugi, Ikeda; Hideaki Yamanada, Hirakata; Kohji Kawabata, Osaka, all of Japan

[73] Assignee: Fujisawa Pharmaceutical Co., Ltd., Osaka, Japan

[21] Appl. No.: 655,458

[22] Filed: Sep. 28, 1984

[51] Int. Cl.$^4$ .................. C07D 501/22; A61K 31/545
[52] U.S. Cl. .................................................. 540/215
[58] Field of Search ........................ 544/16; 540/215

[56] References Cited

FOREIGN PATENT DOCUMENTS 1391806 4/1975 United Kingdom .

OTHER PUBLICATIONS

Barton and Ollis, Comprehensive Organic Chemistry, vol. 2, Pergamon, New York, (1979), pp. 1151, 1162.
Chernywk et al., "Synthesis and Properties of Phosphonium . . . Salts . . . ", Chem. Abst. 83:179223p, (1975).

*Primary Examiner*—Nicholas S. Rizzo
*Attorney, Agent, or Firm*—Oblon, Fisher, Spivak, McClelland & Maier

[57] ABSTRACT

The invention relates to a process for the preparation of 3-phosphoniummethyl-3-cephem compounds of the formula:

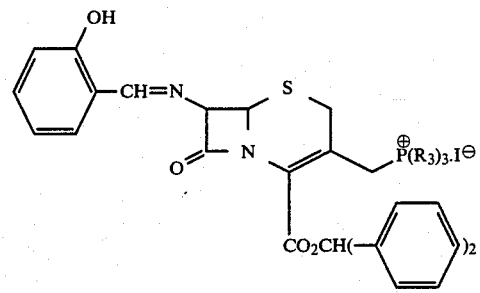

wherein $R_3$ is aryl, or a salt thereof, which is characterized by reacting one equimolar amount of a 3-hydroxymethyl-3-cephem compound of the formula:

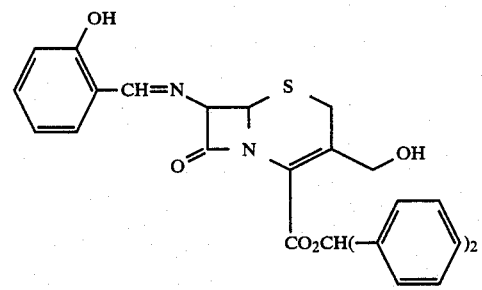

or a salt thereof, with two or a little over two equimolar amount of triarylphosphine and one or a little over one equimolar amount of iodine, said prepared compounds being useful as intermediates for manufacturing 3-vinyl-3-cephem compounds possessing potent antimicrobial activities.

2 Claims, No Drawings

PROCESS FOR THE PREPARATION OF 3-PHOSPHONIUMMETHYL-3-CEPHEM COMPOUNDS

The present invention relates to a novel process for the preparation of 3-phosphoniummethyl-3-cephem compounds.

More particularly, it relates to a novel process for the preparation of 3-phosphoniummethyl-2-cephem compounds from 3-hydroxymethyl-3-cephem compounds by single step synthesis.

Accordingly, the object of the present invention is to provide 3-phosphoniummethyl-3-cephem compounds in high yield.

In the past, the 3-phosphoniummethyl-3-cephem compounds were prepared from 3-hydroxymethyl-3-cephem compounds through 3-chloromethyl-3-cephem compounds.

The inventors of the present invention have succeeded for the first time in the preparation of 3-phosphoniummethyl-3-cephem compounds from 3-hydroxymethyl-3-cephem compounds by single step synthesis in high yield.

The process of the present invention is characterized by reacting 3-hydroxymethyl-3-cephem compounds of the formula:

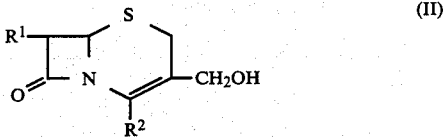

wherein
$R^1$ is amino or a protected amino group, and
$R^2$ is carboxy or a protected carboxy group,
or a salt thereof, with triarylphosphine and iodine to give 3-phosphoniummethyl-3-cephem compounds of the formula:

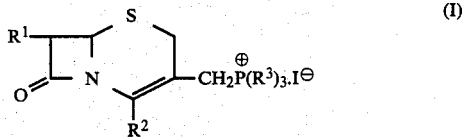

wherein
$R^3$ is aryl, and
$R^1$ and $R^2$ are each as defined above,
or a salt thereof.

The 3-phosphoniummethyl-3-cephem compounds obtained by the process of the present invention are useful as intermediates for manufacturing 3-vinyl-3-cephem compounds possessing potent antimicrobial activities.

In the above description of the present specification, suitable examples and illustration of the definitions for $R^1$, $R^2$ and $R^3$ are explained in detail as follows.

The term "lower" used in the present specification is intended to mean a group having 1 to 6 carbon atoms, unless otherwise indicated.

Suitable "protected amino" group may include an amino group substituted by a conventional amino-protective group which is used in penicillin and cephalosporin compounds, for example, acyl as mentioned below, ar(lower)alkyl such as mono- (or di or tri)phenyl(lower)alkyl (e.g. benzyl, benzhydryl, trityl, etc.), substituted or unsubstituted ar(lower)alkylidene such as substituted or unsubstituted benzylidene (e.g. benzylidene, salicylidene, etc.), and the like.

Suitable "acyl" may include an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), $(C_3-C_7)$-cycloalkanecarbonyl (e.g. cyclohexanecarbonyl, etc.), and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include ar(lower)alkanoyl such as phenyl(lower)alkanoyl (e.g. phenylacetyl, phenylpropionyl, phenylhexanoyl, etc.), ar(lower)alkoxycarbonyl such as phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, carboxy, protected carboxy as mentioned below, amino, protected amino as mentioned above, carboxy(lower)alkoxyimino (e.g. carboxymethoxyimino, etc.), protected carboxy(lower)alkoxyimino (e.g. methoxycarbonylmethoxyimino, etc.) and the like, and preferable acyl having such substituent(s) may be mono (or di or tri)halo(lower)alkanoyl (e.g. chloroacetyl, bromoacetyl, dichloroacetyl, trifluoroacetyl, etc.), mono (or di or tri)-halo(lower)alkoxycarbonyl (e.g. chloromethoxycarbonyl, dichloromethoxycarbonyl, 2,2,2-tri-chloroethoxycarbonyl, etc.), nitro- (or halo or lower alkoxy)-phenyl(lower)alkoxycarbonyl (e.g. nitrobenzyloxycarbonyl, chlorobenzyloxycarbonyl, methoxybenzyloxycarbonyl, etc.), amino- and carboxy-substituted lower alkanoyl (e.g. 5-amino-5-carboxypentanoyl, etc.), protected amino- and protected carboxy-substituted lower alkanoyl (e.g. 5-benzoylamino-5-benzhydryloxycarbonyl-pentanoyl, etc.), and the like.

Suitable "protected carboxy" group may include an esterified carboxy group which is conventionally used in pencillin or cephalosporin compounds at their 3rd or 4th position thereof.

Suitable "ester moiety" in "esterified carboxy group" may include lower alkyl ester (e.g. methyl ester, ethyl ester, propyl ester, isopropyl ester, butyl ester, isobutyl ester, t-butyl ester, pentyl ester, tertpentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester isopropylthiomethyl ester, etc.), mono (or di or tri)halo(lower)alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, isobutyryloxymethyl ester, valeryloxymethyl ester, pivaloyloxymethyl ester, hexanoyloxymethyl ester, 2-acetoxyethyl ester, 2-propionyloxyethyl ester, 1-acetoxypropyl ester, etc.), lower alkanesulfonyl(lower)alkyl ester (e.g. mesylmethyl ester, 2-mesylethyl ester, etc.), ar(lower)alkyl ester which may have one or more substituent(s) such as mono (or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), heterocyclic ester (e.g. phthalidyl ester, etc.), and the like.

Suitable aryl may include phenyl, tolyl, xylyl, mesityl, cumenyl and the like.

Suitable salt of the starting compound (II) and the object compound (I) may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); and the like.

The process of the present invention can be illustrated by the following reaction scheme.

(II)

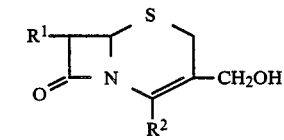

or a salt thereof

| Triarylphosphine and Iodine ↓

-continued (I)

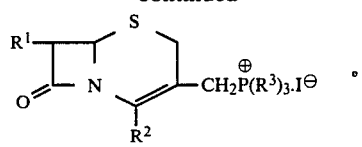

or a salt thereof wherein $R^1$, $R^2$ and $R^3$ are each as defined above.

In the process of the present invention, amounts of triarylphosphine and iodine are not restrictive. However, in order to obtain the object compound (I) in high yield, the reaction may preferably be carried out using an amount of one or more equimolar, more preferably two or a little over two equimolar triarylphosphine and also using an amount of one or a little over one equimolar iodine with the starting compound (II).

This process may be carried out in the presence of a conventional solvent which does not adversely influence the reaction such as N,N-dimethylformamide, N,N-dimethylacetamide, dichloromethane, dichloroethane, chloroform, tetrahydrofuran, dioxane, etc., or a mixture thereof.

The reaction temperature of this process is not restrictive, and the reaction is preferably carried out from under ice-cooling to at ambient temperature which is much advantageous in the manufacture of the object 3-phosphoniummethyl-3-cephem compounds.

The 3-phosphoniummethyl-3-cephem compounds obtained by the process of the present invention are useful as intermediates for manufacturing 3-vinyl-3-cephem compounds, which possess potent antimicrobial activities, for example, as shown in the following reaction schemes.

(A)

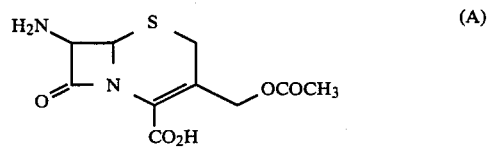

Step 1 | 1. Deacetylation by an aqueous sodium hydroxide
2. Salicyaldehyde
3. Esterification by diphenyldiazomethane
↓

(II)

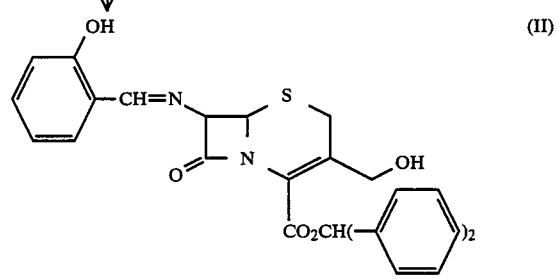

Process of the present invention (Step 2) | Triphenylphosphine and Iodine
↓

-continued

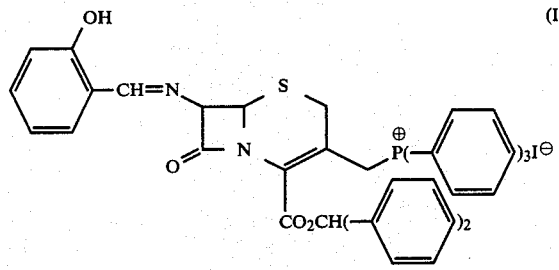
(I)

Step 3 | Vinylation by an aqueous formaldehyde in the presence of potassium carbonate

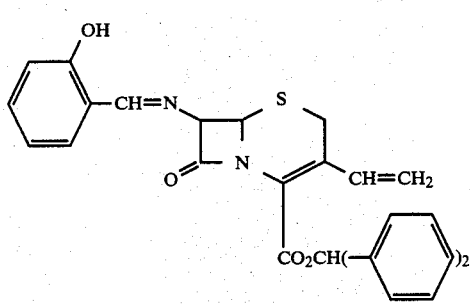
(B)

Step 4 | Removal of the salicylidene group by hydrochloric acid

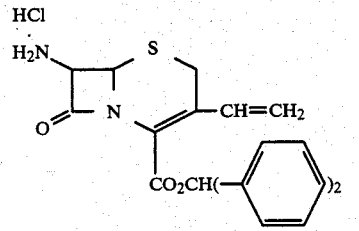
(C)

Step 5 | 1. ClCH₂CCCOCl  
2. Thiourea

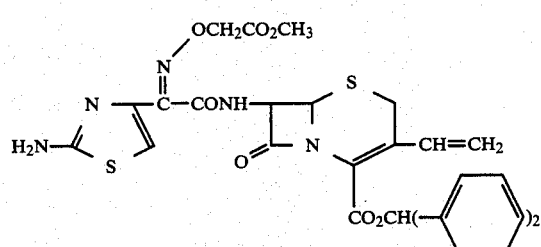
(D)

Step 6 | 1. Removal of the benzhydryl ester group by Boron trifluoride etherate  
2. Removal of the methyl ester group by an aqueous sodium hydroxide -continued

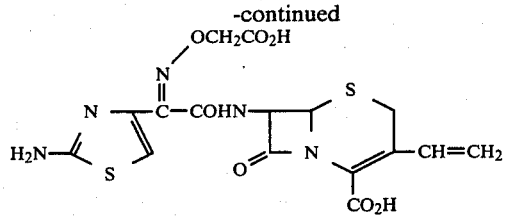
(E)

In the steps 2 and 3 in the above reaction schemes, the compound (B) can be prepared from the compound (II) with or without isolation of the compound (I), and in the industrial sense, these steps can preferably be carried out in one pot without isolation and purification of the compound (I).

The final compound (E) thus obtained possesses potent antimicrobial activities and is useful as antimicrobial agents, especially for oral administration.

The following examples are given for the purpose of illustrating the present invention.

EXAMPLE 1

To a solution of benzhydryl (6R,7R)-3-hydroxymethyl-8-oxo-7-salicylideneamino-5-thia-1-azabicyclo[4.2.0]oct-2-ene-2-carboxylate (33 g) and triphenylphosphine (37.2 g) in N,N-dimethylformamide (90 ml) was added dropwise a solution of iodine (19.5 g) in tetrahydrofuran (30 ml) at 15° C., and the mixture was stirred for 15 minutes. The reaction mixture was poured into isopropyl alcohol (1200 ml) and then stirred for 2 hours. The precipitated crystals were collected by filtration to give (6R,7R)-2-benzhydryloxycarbonyl-8-oxo-7-salicylideneamino-5-thia-1-azabicyclo[4.2.0]oct-2-ene-3-ylmethyl-triphenyl-phosphonium iodide almost quantitatively.

IR(Nujol): 1780, 1715, 1620, 1250 cm$^{-1}$.

NMR(DMSO, δ): 3.5–3.9 (2H, m), 4.8–5.6 (2H, m), 5.61 (1H, d, J=5 Hz), 5.83 (1H, d, J=5 Hz), 6.30 (1H, s), 6.8–8.2(29H, m), 8.88 (1H, s), 12.16 (1H, s).

This product was dissolved in dichloromethane (600 ml), and thereto was added isopropyl alcohol (150 ml) and then 36% aqueous formaldehyde (150 ml), keeping the pH value to 8.5 to 8.7 with 20% aqueous potassium carbonate. After stirring for 2 hours at 23° to 25° C., the organic layer was separated, washed with water and an aqueous sodium chloride, and then concentrated. The concentrate was allowed to stand for 2 hours under ice-cooling, and the precipitated product was collected by filtration and washed with isopropyl alcohol and petroleum ether to give benzhydryl (6R, 7R)-8-oxo-7-salicylideneamino-3-vinyl-5-thia-1-azabicyclo[4.2.0]oct-2-ene-2-carboxylate (17.1 g).

IR(Nujol): 1770, 1710, 1620, 1580(s) cm$^{-1}$.

EXAMPLE 2

To a mixture of benzhydryl (6R, 7R)-3-hydroxymethyl-8-oxo-7-salicylideneamino-5-thia-1-azabicyclo[4.2.0]oct-2-ene-2-carboxylate (312 g) and triphenylphosphine (360 g) in N,N-dimethylacetamide (940 ml) was added iodine (190 g) portionwise with stirring, keeping the temperature under 20° C., and the reaction mixture was stirred for 40 minutes at the same condition to prepare a solution containing (6R, 7R)-2-benzhydryloxycarbonyl-8-oxo-7-salicylideneamino-5-thia-1-azabicyclo[4.2.0]oct-2-ene-3-ylmethyl-triphenyl-phosphonium iodide.

To a stirred mixture of dichloromethane(4.5 liter) and 36% aqueous formaldehyde (1 liter) was added dropwise the above obtained solution, adjusting to pH 8.5-9.0 with an aqueous sodium hydroxide. After stirring for 45 minutes at 25°-30° C., the reaction mixture was adjusted to pH 7.0-7.5 with an aqueous hydrochloric acid, and washed with water. The separated organic layer was concentrated to one third volume. To this concentrate was added methanol (2 liter) and the precipitated crystals were collected by filtration, washed with methanol (600 ml) and dried in vacuo to give benzhydryl (6R, 7R)-8-oxo-7-salicylideneamino-3-vinyl-5-thia-1-azabicyclo[4.2.0]oct-2-ene-2-carboxylate (200 g).

EXAMPLE 3

To a solution of triphenylphosphine (11.6 g) in N,N-dimethylformamide (40 ml) was added iodide (5.1 g) under ice-cooling with stirring. After stirring at 5° C. for 30 minutes, thereto was added benzhydryl (6R, 7R)-3-hydroxymethyl-8-oxo-7-benzoylamino-5-thia-1-azabicyclo[4.2.0]oct-2-ene-2-carboxylate (10 g) and then the mixture was stirred at 5° C. for 30 minutes and at 25° C. for additional 30 minutes. The reaction mixture was poured into a mixture of dichloromethane and water, and the separated organic layer was washed with water and concentrated to give a solution containing (6R, 7R)-2-benzhydryloxycarbonyl-8-oxo-7-benzoylamino-5-thia-1-azabicyclo[4.2.0]oct-2-ene-3-ylmethyl-triphenyl-phosphonium iodide.

To this solution were added 36% aqueous formaldehyde (50 ml) and water (50 ml), and the mixture was adjusted to pH 8.5 to 8.7 with 20% aqueous potassium carbonate. After stirring at 20° to 25° C. for 2 hours, to the reaction mixture was added isopropyl alcohol (100 ml) and stirred under ice-cooling for an hour. The precipitated product was collected by filtration and washed with isopropyl alcohol and diisopropyl ether to give benzhydryl (6R, 7R)-8-oxo-7-benzoylamino-3-vinyl-5-thia-1-azabicyclo[4.2.0]oct-2-ene-2-carboxylate (4.9 g).

IR(Nujol): 3340, 1790, 1720, 1653 cm$^{-1}$.

EXAMPLE 4

To a solution of triphenylphosphine (7.1 g) in N,N-dimethylformamide (50 ml) was added iodide (3.1 g) under ice-cooling with stirring. After stirring at 5° C. for 30 minutes, thereto was added benzhydryl (6R, 7R)-3-hydroxymethyl-8-oxo-7-(5-benzoylamino-5-benzhydryloxycarbonylpentanoylamino)-5-thia-1-azabicyclo[4.2.0]oct-2-ene-2-carboxylate (10 g) and then the mixture was stirred at 5° C. for 15 minutes and at 25° C. for additional 20 minutes. The reaction mixture was poured into a mixture of dichloromethane and water, and the separated organic layer was washed with water and concentrated to give a solution containing (6R, 7R)-2-benzhydryloxycarbonyl-8-oxo-7-(5-benzoylamino-5-benzhydryloxycarbonylpentanoylamino)-5-thia-1-azabicyclo[4.2.0]oct-2-ene-3-ylmethyl-triphenyl-phosphonium iodide.

To this solution were added 36% aqueous formaldehyde (30 ml) and water (50 ml), and the mixture was adjusted to pH 8.5 to 8.7 with 20% aqueous potassium carbonate. After stirring at 25° C. for 1.5 hours, to the reaction mixture was added methanol (50 ml) and stirred under ice-cooling for an hour. The precipitated product was collected by filtration and washed with methanol and diisopropyl ether to give benzhydryl (6R, 7R)-8-oxo-7-(5-benzoylamino-5-benzhydryloxycarbonylpentanoylamino)-3-vinyl-5-thia-1-azabicyclo[4.2.0]oct-2-ene-2-carboxylate (5.1 g).

IR(Nujol): 3300, 1770, 1730, 1710, 1650 cm$^{-1}$.

What we claim is:

1. A process for the preparation of a 3-phosphoniummethyl-3-cephem compound of the formula:

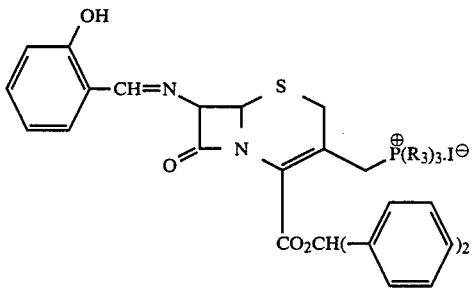

wherein $R_3$ is aryl, or a salt thereof, which is characterized by reacting one equimolar amount of a 3-hydroxymethyl-3-cephem compound of the formula:

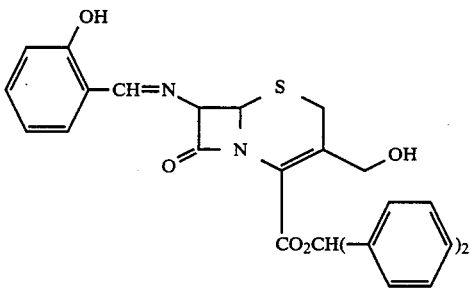

or a salt thereof, with two or a little over two equimolar amount of triarylphosphine and one or a little over one equimolar amount of iodine.

2. The process of claim 1 wherein $R_3$ is phenyl.